(12) United States Patent
Taniguchi et al.

(10) Patent No.: US 10,940,144 B2
(45) Date of Patent: Mar. 9, 2021

(54) DRUG CONTAINING PYRIDYLAMINOACETIC ACID COMPOUND

(71) Applicant: SANTEN PHARMACEUTICAL CO., LTD., Osaka (JP)

(72) Inventors: Takazumi Taniguchi, Ikoma (JP); Takahiro Akaishi, Ikoma (JP); Hitoshi Nakazawa, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/640,573

(22) PCT Filed: Sep. 27, 2018

(86) PCT No.: PCT/JP2018/035931
§ 371 (c)(1),
(2) Date: Feb. 20, 2020

(87) PCT Pub. No.: WO2019/065838
PCT Pub. Date: Apr. 4, 2019

(65) Prior Publication Data
US 2020/0188377 A1 Jun. 18, 2020

(30) Foreign Application Priority Data
Sep. 29, 2017 (JP) .............................. JP2017-190757

(51) Int. Cl.
*A61K 31/444* (2006.01)
*A61K 31/4439* (2006.01)
*A61P 27/02* (2006.01)
*A61K 9/00* (2006.01)

(52) U.S. Cl.
CPC ........ *A61K 31/4439* (2013.01); *A61K 9/0048* (2013.01); *A61P 27/02* (2018.01)

(58) Field of Classification Search
CPC .............................. A61K 31/444; A61P 27/02
USPC ........................................................ 514/333
See application file for complete search history.

(56) References Cited

U.S. PATENT DOCUMENTS

| 8,685,986 | B2 * | 4/2014 | Hagihara | A61K 31/506 514/256 |
| 9,415,038 | B2 * | 8/2016 | Shams | A61K 31/444 |
| 2004/0192699 | A1 | 9/2004 | Miyawaki et al. | |
| 2011/0054172 | A1 | 3/2011 | Iwamura et al. | |
| 2012/0190852 | A1 | 7/2012 | Hagihara et al. | |
| 2014/0018350 | A1 | 1/2014 | Kirihara et al. | |
| 2014/0018396 | A1 | 1/2014 | Kirihara et al. | |
| 2014/0113907 | A1 | 4/2014 | Iwamura et al. | |
| 2015/0196541 | A1 | 7/2015 | Shams et al. | |
| 2016/0317512 | A1 | 11/2016 | Endo | |
| 2016/0317664 | A1 | 11/2016 | Endo | |
| 2016/0324838 | A1 | 11/2016 | Shams et al. | |
| 2017/0114043 | A1 | 4/2017 | Yamamoto et al. | |
| 2017/0121288 | A1 | 5/2017 | Yamamoto et al. | |
| 2018/0169079 | A1 | 6/2018 | Shams et al. | |
| 2018/0185489 | A1 | 7/2018 | Miyazaki et al. | |
| 2018/0200239 | A1 | 7/2018 | Kirihara et al. | |
| 2019/0105310 | A1 | 4/2019 | Shams et al. | |

FOREIGN PATENT DOCUMENTS

| JP | 2001072591 A | 3/2001 |
| WO | 03004058 A1 | 1/2003 |
| WO | 2009113600 A1 | 9/2009 |
| WO | 2015105144 A1 | 7/2015 |
| WO | 2017002941 A1 | 1/2017 |
| WO | 2017006985 A1 | 1/2017 |

OTHER PUBLICATIONS

Barkana et al., "Neuroprotection in ophthalmology: a review", Brain Res Bull., 2004, 62(6), pp. 447-453.
Ciancaglini, et al., "Perfusion of the optic nerve head and visual field damage in glaucomatous patients", Graefes. Arch. Clin. Exp. Ophthalmol., 2001, 239, pp. 549-555.
Drago, et al., "Latanoprost Exerts Neuroprotective Activity in vitro and in vivo", Exp. Eye Res., 2001, 72, pp. 479-486.
International Search Report (PCT/ISA/210) and an English translation thereof, and Written Opinion (PCT/ISA/237) dated Jan. 8, 2019, by the Japanese Patent Office as the International Searching Authority for International Application No. PCT/JP2018/035931.
Mori, et al., "Stimulation of prostanoid IP and EP2 receptors dilates retinal arterioles and increases retinal and choroidal blood flow in rats", European Journal of Pharmacology, 570, 2007, pp. 135-141.
Mori, et al., "The prostanoid EP2 receptor agonist ONO-AE1-259-01 protects against glutamate-induced neurotoxicity in rat retina", European Journal of Pharmacology, Aug. 2009, vol. 616, pp. 64-67.
Sasaoka, et al., "Intravitreal injection of endothelin-1 caused optic nerve damage following to ocular hypoperfusion in rabbits", Exp. Eye Res., 2006, 83, pp. 629-637.

(Continued)

*Primary Examiner* — Charanjit Aulakh
(74) *Attorney, Agent, or Firm* — Buchanan Ingersoll & Rooney PC

(57) ABSTRACT

The present invention aims to find a novel pharmaceutical use of omidenepag, esters thereof, or salts thereof. The present inventors have made intensive studies to find a novel pharmaceutical use of omidenepag, an ester thereof, or a salt thereof, and have found as a result that omidenepag, an ester thereof, or a salt thereof significantly dilates retinal blood vessels, and significantly increases blood flow. Therefore, omidenepag, an ester thereof, or a salt thereof is expected to protect retinal nerve cells and be useful for prevention and/or treatment of ophthalmic diseases involving retinal nerve cell disorder.

16 Claims, No Drawings

(56) References Cited

OTHER PUBLICATIONS

Yaoeda, et al., "Relationship between optic nerve head microcirculation and visual field loss in glaucoma", Acta. Ophthalmol. Scand., 2003, 81, pp. 253-259.

Misfeldt, et al., "Perivascular Cells With Pericyte Characteristics Are Involved in ATP- and $PGE_2$-Induced Relaxation of Porcine Retinal Arterioles In Vitro", Physiology and Pharmacology, Investigative Ophthalmology & Visual Science, 2013, vol. 54, No. 0, pp. 3258-3264.

* cited by examiner

DRUG CONTAINING PYRIDYLAMINOACETIC ACID COMPOUND

TECHNICAL FIELD

The present invention relates to a retinal nerve cell protecting agent or a retinal blood flow improving agent containing omidenepag, an ester thereof, or a salt thereof as an active ingredient.

BACKGROUND ART

The retina is a tissue with a thickness of about 0.1 to 0.5 mm, including 10 layers of the inner limiting membrane, the nerve fiber layer, the ganglion cell layer, the inner plexiform layer, the inner nuclear layer, the outer plexiform layer, the outer nuclear layer, the outer limiting membrane, the photoreceptor layer, and the retinal pigment epithelium. In the retina, there are retinal nerve cell groups called photoreceptor cells, bipolar cells, ganglion cells, horizontal cells, amacrine cells, and Muller cells.

Retinal nerve cells play an important role in the reception and transmission of visual information, such as conversion of optical stimulation into an electrical signal and transmission of the electrical signal to the brain.

Here, the transmission mechanism is described in detail. Visual information from the eye is converted into an electrical signal by photoreceptor cells, and the electrical signal passes through horizontal cells, bipolar cells, and/or amacrine cells, and then is transmitted to ganglion cells. Subsequently, the electrical signal is transmitted to the brain via the optic nerve, which is a bundle of optic nerve fibers containing ganglion cell axons.

For this reason, when retinal nerve cells are damaged, transmission of visual information to the brain is blocked, resulting in visual field impairment. It is widely known that visual field impairment with functional breakdown of retinal nerve cells occurs in, for example, various retinal diseases such as retinal vascular occlusion, diabetic retinopathy, ischemic optic neuropathy, glaucoma, macular degeneration, retinitis pigmentosa, and Leber's disease (Non Patent Literature 1).

Meanwhile, in retinal nerve cells, oxygen and nutrient supply, gas exchange, and removal of other metabolites take place through the retinal blood flow, and blood circulation in the retina is greatly involved in the development of diabetic retinopathy and glaucoma.

In fact, glaucoma patients are observed to have a positive correlation between the decrease in blood flow in the retina (optic nerve head) and the degree of visual field impairment (Non Patent Literatures 2 and 3).

Furthermore, a study in rabbits suggests that a decrease in blood flow in the retina caused by endothelin-1 induces a decrease in retinal nerve cells (Non Patent Literature 4). Thus, the decrease in blood flow in the retina is thought to cause various diseases due to the functional breakdown of retinal nerve cells.

Therefore, it is considered that the improvement of blood flow in the retina has a function of protecting retinal nerve cells, and various studies have been made so far to apply a medicament aimed at improving retinal blood flow, such as a calcium channel blocker, to the treatment of ophthalmic diseases caused by retinal nerve cell disorders.

In addition, for use in the treatment of ophthalmic diseases caused by retinal nerve cell disorder, various studies are conducted also on medicaments that may directly inhibit retinal nerve cell disorder, such as glutamate neurotoxicity inhibitors, antioxidants, anti-inflammatory agents, neurotrophic factors, protease inhibitors, and NO synthesis inhibitors.

So far, as examples of the above, Patent Literature 1 discloses a retinal nerve cell protecting agent containing nipradilol, which is one of β-blockers, as an active ingredient, Patent Literature 2 discloses a retinal ganglion cell protecting agent containing an $\alpha_1$-receptor blocker such as bunazosin hydrochloride as an active ingredient, and Non Patent Literature 5 discloses e.g. the neuroprotective action of latanoprost, which is one of prostaglandin derivatives.

It is known that ONO-AE1-259-01, which is an EP2 receptor agonist, dilates retinal blood vessels and has a retinal neuroprotective action (Non Patent Literature 6 and Non Patent Literature 7).

Meanwhile, omidenepag is described as one of an enormous number of pyridylaminoacetic acid compounds in Patent Literature 3 and Patent Literature 4. In addition, it is stated that these pyridylaminoacetic acid compounds have an EP2 agonistic action (Patent Literature 4), and thus are expected to have an intraocular pressure lowering action and can be a therapeutic agent for glaucoma (Patent Literature 3).

Moreover, Patent Literatures 5 and 6 state that the intraocular pressure lowering action is enhanced by combining omidenepag with another glaucoma therapeutic agent such as timolol, Patent Literature 7 states that omidenepag at a specific content exhibits a particularly excellent intraocular pressure lowering action, and Patent Literature 8 states that omidenepag is useful as a therapeutic agent for diseases accompanied by highly elevated intraocular pressure.

In addition, Patent Literatures 9 to 11 describe specific formulations containing omidenepag as an active ingredient.

Note that the entire contents of Patent Literatures 1 to 11 and the other literatures described in the present specification are incorporated as the disclosure of the present specification.

However, none of the literatures describes the retinal vasodilatory action, retinal nerve cell protecting action, and retinal blood flow improving action of omidenepag, an ester thereof, or a salt thereof.

CITATION LIST

Patent Literatures

Patent Literature 1: Japanese Patent Application Publication No. 2001-072591
Patent Literature 2: International Publication No. WO2003/004058
Patent Literature 3: Unites States Patent Application Publication No. 2012/0190852
Patent Literature 4: Unites States Patent Application Publication No. 2011/0054172
Patent Literature 5: Unites States Patent Application Publication No. 2014/0018396
Patent Literature 6: Unites States Patent Application Publication No. 2014/0018350
Patent Literature 7: Unites States Patent Application Publication No. 2015/0196541
Patent Literature 8: International Publication No. WO2017/006985
Patent Literature 9: Unites States Patent Application Publication No. 2016/0317512

Patent Literature 10: Unites States Patent Application Publication No. 2016/0317664
Patent Literature 11: International Publication No. WO2017/002941

Non Patent Literatures

Non Patent Literature 1: Brain Res Bull., 2004, 62(6), 447-453
Non Patent Literature 2: Graefes. Arch. Clin. Exp. Ophthalmol., 2001, 239, 549-555.
Non Patent Literature 3: Acta. Ophthalmol. Scand., 2003, 81, 253-259.
Non Patent Literature 4: Exp. Eye Res., 2006, 83, 629-637.
Non Patent Literature 5: Exp. Eye Res., 2001, 72, 479-486
Non Patent Literature 6: Eur. J. Pharmacol., 2007, 570, 135-141
Non Patent Literature 7: Eur. J. Pharmacol., 2009, 616, 64-67

SUMMARY OF INVENTION

Problems to be Solved by the Invention

To find a novel pharmaceutical use of omidenepag, esters thereof, or salts thereof is a very interesting task.

Means for Solution of the Problems

With the above in mind, the present inventors have made intensive studies to find a novel pharmaceutical use of omidenepag, an ester thereof, or a salt thereof, and have found as a result that omidenepag, an ester thereof, or a salt thereof can significantly dilate retinal blood vessels as compared with other EP2 agonists, and thereby significantly increase blood flow. This finding has led to the completion of the present invention. Specifically, the present invention provides the following.

Another aspect of the present invention may be as follows.

[1]
A medicament for retinal vasodilatory action, retinal nerve cell protection, and/or retinal blood flow improvement, comprising omidenepag, an ester thereof, or a salt thereof as an active ingredient.

[2]
The medicament according to [1] described above, wherein the medicament is a medicament for protecting a retinal nerve cell, and the retinal nerve cell is a photoreceptor cell, a bipolar cell, a retinal ganglion cell, a horizontal cell, or an amacrine cell.

[3]
The medicament according to [1] described above, wherein the medicament is a medicament for improving retinal blood flow.

[4]
The medicament according to any one of [1] to [3] described above, wherein a content of the omidenepag, the ester thereof, or the salt thereof is 0.000001 to 30% (w/v).

[5]
The medicament according to [4] described above, wherein the content of the omidenepag, the ester thereof, or the salt thereof is 0.0015 to 10% (w/v).

[6]
The medicament according to [4] described above, wherein the content of the omidenepag, the ester thereof, or the salt thereof is 0.002% (w/v).

[7]
The medicament according to any one of [1] to [6] described above, wherein the omidenepag, the ester thereof, or the salt thereof is omidenepag isopropyl.

[8]
The medicament according to any one of [1] to [7] described above, wherein a route of administration is ophthalmic administration, intravitreal administration, conjunctival sac administration, intracameral administration, subconjunctival administration, subtenon administration, or punctal plug administration.

[9]
The medicament according to [8] described above, wherein the route of administration is ophthalmic administration or intravitreal administration.

[10]
A medicament for retinal vasodilatory action, retinal nerve cell protection, and/or retinal blood flow improvement, comprising omidenepag, an ester thereof, or a salt thereof as an active ingredient, wherein
a content of the omidenepag, the ester thereof, or the salt thereof is 0.0015 to 10% (w/v), and
a route of administration is ophthalmic administration or intravitreal administration.

[11]
A medicament for retinal vasodilatory action, retinal nerve cell protection, and/or retinal blood flow improvement, comprising omidenepag, an ester thereof, or a salt thereof as an active ingredient, wherein
a content of the omidenepag, the ester thereof, or the salt thereof is 0.002% (w/v), and
a route of administration is ophthalmic administration.

[12]
The medicament according to any one of [1] to [11] described above, which is used for prevention and/or treatment of an ophthalmic disease.

[13]
The medicament according to [12] described above, wherein the ophthalmic disease is an ophthalmic disease involving retinal nerve cell disorder and/or retinal blood flow.

[14]
The medicament according to [12] or [13] described above, wherein the ophthalmic disease is visual field abnormality, retinal vascular occlusion, diabetic retinopathy, ischemic optic neuropathy, glaucoma, glaucomatous optic neuropathy, glaucomatous visual field stenosis, glaucomatous optic nerve atrophy, PPG (Preperimetoric glaucoma), optic neuropathy caused by insufficiency of blood circulation, macular degeneration, retinitis pigmentosa, Leber's disease, retinopathy of prematurity, retinal detachment, or retinal pigment epithelial detachment.

[15]
Omidenepag, an ester thereof, or a salt thereof for use in prevention and/or treatment of an ophthalmic disease.

[16]
A method of preventing and/or treating an ophthalmic disease, comprising administering to a patient a medicament containing omidenepag, an ester thereof, or a salt thereof as an active ingredient.

[17]
The method according to [16], wherein the ophthalmic disease is an ophthalmic disease involving retinal nerve cell disorder and/or retinal blood flow.

[18]
A method of producing a medicament for retinal vasodilatory action, retinal nerve cell protection, and/or retinal blood flow improvement, comprising formulating omidenepag, an ester thereof, or a salt thereof as an active ingredient.

[19]

Use of omidenepag, an ester thereof, or a salt thereof for producing a medicament for retinal vasodilatory action, retinal nerve cell protection, and/or retinal blood flow improvement.

Note that two or more of the configurations [1] to [19] can be arbitrarily selected and combined.

Advantageous Effects of Invention

As described in detail in Examples below, it has been found that omidenepag, an ester thereof, or a salt thereof can significantly dilate retinal blood vessels as compared with other EP2 agonists. As the retinal blood vessels dilate, the blood flow rate of the retinal blood vessels can be significantly increased, and it can thus be understood that omidenepag, an ester thereof, or a salt thereof is useful as a retinal nerve cell protecting agent and/or a retinal blood flow improving agent, and is therefore useful for the prevention or treatment of ophthalmic diseases involving retinal nerve cell disorders.

DESCRIPTION OF EMBODIMENTS

Hereinafter, embodiments of the present invention are described in detail.

[Medicament]

The omidenepag contained in the medicament for retinal vasodilation, retinal nerve cell protection, and/or retinal blood flow improvement according to the present invention (retinal vasodilator, retinal nerve cell protecting agent, and/or retinal blood flow improving agent, or simply referred to as a "medicament") is a compound represented by the following formula (1) (CAS registration number: 1187451-41-7):

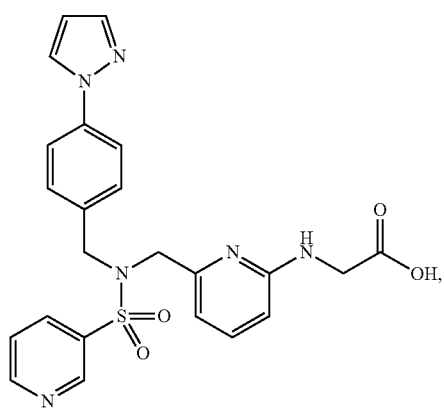

(1)

and is also referred to as (6-{[4-(pyrazol-1-yl)benzyl](pyridin-3-ylsulfonyl)aminomethyl}pyridin-2-ylamino)acetic acid.

The ester of omidenepag contained in the medicament of the present invention is preferably an ester formed by dehydration condensation of a carboxyl group of omidenepag with a monohydric alcohol having 1 to 6 carbon atoms, and suitably an ester formed by dehydration condensation of a carboxyl group of omidenepag with a monohydric alcohol more preferably having 2 to 5 carbon atoms and further preferably having 3 or 4 carbon atoms. Specific esters include methyl esters, ethyl esters, n-propyl esters, isopropyl esters, n-butyl esters, isobutyl esters, sec-butyl esters, tert-butyl esters, n-pentyl esters, and n-hexyl esters, more preferably ethyl esters, n-propyl esters, isopropyl esters, and more preferably isopropyl esters. A specific isopropyl ester of omidenepag is a compound represented by the following formula (2) (CAS registration number: 1187451-19-9):

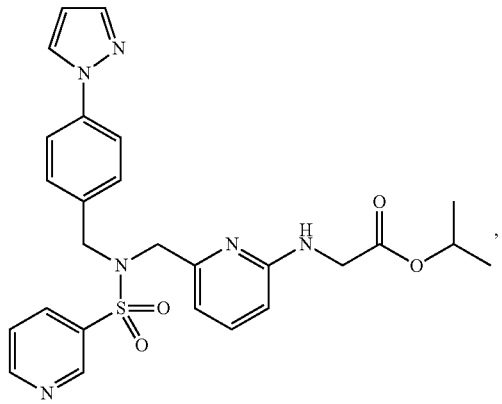

(2)

and is also referred to as omidenepag isopropyl or isopropyl (6-{[4-(pyrazol-1-yl)benzyl](pyridin-3-ylsulfonyl)aminomethyl}pyridin-2-ylamino)acetate.

The salt of omidenepag or ester salt of omidenepag contained in the medicament of the present invention is not particularly limited as long as it is a pharmacologically acceptable salt. Specific examples include inorganic acid salts such as hydrochlorides, hydrobromides, hydroiodides, nitrates, sulfates, and phosphates; organic acid salts such as acetates, trifluoroacetates, benzoates, oxalates, malonates, succinates, maleates, fumarates, tartrates, citrates, methanesulfonates, ethanesulfonates, trifluoromethane sulfonates, benzene sulfonates, p-toluene sulfonates, glutamates, and aspartates; metal salts such as sodium salts, potassium salts, calcium salts, and magnesium salts; inorganic salts such as ammonium salts; and organic amine salts such as triethylamine salts or guanidine salts, and preferably include hydrochlorides and trifluoroacetates.

The omidenepag, the ester thereof, or the salt thereof contained in the medicament of the present invention can be produced according to e.g. a normal method in the technical field and the methods described in Unites States Patent Application Publication No. 2012/0190852 (Patent Literature 3), Unites States Patent Application Publication No. 2011/0054172 (Patent Literature 4), Unites States Patent Application Publication No. 2017/0121288, and Unites States Patent Application Publication No. 2017/0114043. In the production methods, the scope of the content of omidenepag, an ester thereof, or a salt thereof contained in the medicament of the present invention, the type and amount of the additive, the route of administration, and the like can employ the modes as described in the above literatures. Note that the term "omidenepag, an ester thereof, or a salt thereof" used in the present application is meant to include (1) omidenepag, (2) an ester of omidenepag, (3) a salt of omidenepag, and (4) an ester salt of omidenepag.

The content of omidenepag, an ester thereof, or a salt thereof contained in the medicament of the present invention is not particularly limited and depends on the route of administration, and the lower limit thereof is, for example, 0.000001% (w/v), preferably 0.00001% (w/v), more preferably 0.00003% (w/v), 0.0001% (w/v), 0.001% (w/v), 0.01% (w/v), 0.1% (w/v), or 1% (w/v). The upper limit of the above content may be, for example, 30% (w/v), 25% (w/v), 20% (w/v), 15% (w/v), or 12% (w/v), or 0.03% (w/v), 0.01% (w/v), 0.005% (w/v), 0.003% (w/v), or 0.0027% (w/v). More specifically, the above content may be a range formed by combining any of the above lower limits and upper limits, and is, for example, 0.000001 to 30% (w/v), preferably 0.00001 to 25% (w/v), more preferably 0.00003 to 20% (w/v), further preferably 0.0001 to 15% (w/v), particularly preferably 0.0013 to 12% (w/v), especially preferably 0.0015 to 10% (w/v), and most preferably 0.002% (w/v). Here, "% (w/v)" means the mass (g) of an active ingredient (omidenepag, an ester thereof, or a salt thereof) or an additive (such as a surfactant) contained in 100 mL of the medicament. For example, omidenepag at 0.01% (w/v) means that the content of omidenepag contained in 100 mL of the medicament is 0.01 g.

When the medicament of the present invention is an ophthalmic solution, the lower limit of the content of omidenepag, an ester thereof, or a salt thereof contained in the medicament of the present invention is preferably 0.0003% (w/v), more preferably 0.001% (w/v), further preferably 0.0013% (w/v), and particularly preferably 0.0015% (w/v). In addition, the upper limit of the above content is preferably 0.03% (w/v), more preferably 0.01% (w/v), further preferably 0.005% (w/v), particularly preferably 0.003% (w/v), and especially preferably 0.0027% (w/v). More specifically, the above content may be a range formed by combining any of the above lower limits and upper limits, and is preferably 0.0003 to 0.03% (w/v), more preferably 0.001 to 0.01% (w/v), further preferably 0.001 to 0.005% (w/v), particularly preferably 0.001 to 0.003% (w/v), especially preferably 0.0013 to 0.003% (w/v), and highly especially preferably 0.0015 to 0.0027% (w/v). In further detail, preferable are 0.0010% (w/v), 0.0011% (w/v), 0.0012% (w/v), 0.0013% (w/v), 0.0014% (w/v), 0.0015% (w/v), 0.0016% (w/v), 0.0017% (w/v), 0.0018% (w/v), 0.0019% (w/v), 0.0020% (w/v), 0.0021% (w/v), 0.0022% (w/v), 0.0023% (w/v), 0.0024% (w/v), 0.0025% (w/v), 0.0026% (w/v), 0.0027% (w/v), 0.0028% (w/v), 0.0029% (w/v), 0.0030% (w/v), 0.005% (w/v), 0.01% (w/v), 0.03% (w/v), and a range including the above quantities as the upper limit or the lower limit, and 0.002% (w/v) is most preferable.

When the medicament of the present invention is an ophthalmic injection, the lower limit of the content of omidenepag, an ester thereof, or a salt thereof contained in the medicament of the present invention is preferably 0.000001% (w/v), more preferably 0.000003% (w/v), further preferably 0.000005% (w/v), particularly preferably 0.00001% (w/v), and especially preferably 0.00003% (w/v). In addition, the upper limit of the above content is preferably 30% (w/v), more preferably 10% (w/v), further preferably 1% (w/v), particularly preferably 0.1% (w/v), and especially preferably 0.01% (w/v). More specifically, the above content may be a range formed by combining any of the above lower limits and upper limits, and is preferably 0.000001 to 30% (w/v), more preferably 0.000003 to 10% (w/v), further preferably 0.000005 to 1% (w/v), particularly preferably 0.00001 to 0.1% (w/v), and especially preferably 0.00003 to 0.01% (w/v).

Note that, the case where the medicament of the present invention contains omidenepag or an ester salt thereof means that the content of omidenepag or an ester thereof when the salt is released falls within the above range.

[Additive]

An additive can be used in the medicament of the present invention as necessary. As an additive, for example, it is possible to add surfactants, buffers, tonicity adjusting agents, stabilizers, preservatives, antioxidants, thickeners, bases, pH adjusters, and the like.

The medicament of the present invention can be appropriately blended with a surfactant that can be used as an additive for a pharmaceutical preparation.

Examples of the surfactant include polyoxyethylene castor oils, polyoxyethylene hydrogenated castor oils, polyoxyethylene sorbitan fatty acid esters, vitamin E TPGS, polyoxyethylene fatty acid esters, polyoxyethylene polyoxypropylene glycol, sucrose fatty acid esters, and the like.

More specifically, as the polyoxyethylene castor oils, it is possible to use various polyoxyethylene castor oils having different degrees of polymerization of ethylene oxide, and the degree of polymerization of ethylene oxide is preferably 5 to 100, more preferably 20 to 50, particularly preferably 30 to 40, and most preferably 35. Specific examples of the polyoxyethylene castor oils include polyoxyl 5 castor oil, polyoxyl 9 castor oil, polyoxyl 15 castor oil, polyoxyl 35 castor oil, polyoxyl 40 castor oil, and the like, and polyoxyl 35 castor oil is most preferable.

As the polyoxyethylene hydrogenated castor oils, it is possible to use various polyoxyethylene hydrogenated castor oils having different degrees of polymerization of ethylene oxide, and the degree of polymerization of ethylene oxide is preferably 10 to 100, more preferably 20 to 80, particularly preferably 40 to 70, and most preferably 60. Specific examples of the polyoxyethylene hydrogenated castor oil include polyoxyethylene hydrogenated castor oil 10, polyoxyethylene hydrogenated castor oil 40, polyoxyethylene hydrogenated castor oil 50, polyoxyethylene hydrogenated castor oil 60, and polyoxyethylene hydrogenated castor oil 60 is most preferable.

The polyoxyethylene sorbitan fatty acid esters include Polysorbate 80, Polysorbate 60, Polysorbate 40, polyoxyethylene sorbitan monolaurate, polyoxyethylene sorbitan trioleate, Polysorbate 65, and the like, and Polysorbate 80 is most preferable.

Vitamin E TPGS is also referred to as tocopherol polyethylene glycol 1000 succinate.

The polyoxyethylene fatty acid esters include polyoxyl 40 stearate and the like.

The polyoxyethylene polyoxypropylene glycol includes polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like.

The sucrose fatty acid esters include sucrose stearate ester.

When the medicament of the present invention is blended with a surfactant, the content thereof can be appropriately adjusted depending on the type and the like of the surfactant. Specifically, the lower limit is preferably 0.001% (w/v), more preferably 0.01% (w/v), further preferably 0.1% (w/v), particularly preferably 0.5% (w/v), and most preferably 0.8% (w/v). The upper limit is preferably 10% (w/v), more preferably 5% (w/v), further preferably 4% (w/v), particularly preferably 3% (w/v), and most preferably 2% (w/v). More specifically, the content may be a range formed by combining any of the above lower limits and upper limits, and is preferably 0.001 to 10% (w/v), more preferably 0.01 to 5% (w/v), further preferably 0.1 to 4% (w/v), particularly preferably 0.5 to 3% (w/v), especially preferably 0.5 to 2% (w/v), and most preferably 0.8 to 2% (w/v).

The medicament of the present invention can be appropriately blended with a buffer agent that can be used as an additive for a pharmaceutical preparation.

Examples of the buffer agent include phosphoric acid or a salt thereof, boric acid or a salt thereof, citric acid or a salt thereof, acetic acid or a salt thereof, carbonic acid or a salt thereof, tartaric acid or a salt thereof, F-aminocaproic acid, trometamol, and the like. More specifically, phosphates include sodium phosphate, sodium dihydrogen phosphate, disodium hydrogen phosphate, potassium phosphate, potassium dihydrogen phosphate, dipotassium hydrogen phosphate, and the like, borates include borax, sodium borate, and potassium borate, citric acid or a salt thereof includes citric acid monohydrate, sodium citrate, disodium citrate, trisodium citrate, and the like, acetates include sodium acetate, potassium acetate, and the like, carbonates include sodium carbonate, sodium bicarbonate, and the like, and tartrates include sodium tartrate, potassium tartrate, and the like. Among these, boric acid or a salt thereof, or citric acid or a salt thereof is preferable.

When the medicament of the present invention is blended with a buffer agent, the content thereof can be appropriately adjusted depending on the type and the like of buffering agent, and is preferably 0.001 to 10% (w/v), more preferably 0.01 to 5% (w/v), further preferably 0.1 to 3% (w/v), particularly preferably 0.1 to 2% (w/v), and most preferably 0.2 to 2% (w/v).

The medicament of the present invention can be appropriately blended with a tonicity adjusting agent that can be used as an additive for a pharmaceutical preparation.

Examples of the tonicity adjusting agent include ionic tonicity adjusting agents and nonionic tonicity adjusting agents.

The ionic tonicity adjusting agents include sodium chloride, potassium chloride, calcium chloride, magnesium chloride, and the like, and the nonionic tonicity adjusting agents include glycerin, propylene glycol, sorbitol, mannitol, and the like. When the medicament of the present invention is blended with a tonicity adjusting agent, the content thereof can be appropriately adjusted depending on the type and the like of the tonicity adjusting agent, and is preferably 0.01 to 10% (w/v), more preferably 0.02 to 7% (w/v), further preferably 0.1 to 5% (w/v), particularly preferably 0.5 to 4% (w/v), and most preferably 0.8 to 3% (w/v).

The medicament of the present invention can be appropriately blended with a stabilizer that can be used as an additive for a pharmaceutical preparation.

Examples of the stabilizer include edetic acid, monosodium edetate, disodium edetate, tetrasodium edetate, sodium citrate, and the like, and disodium edetate is particularly preferable. Edetate sodium may be a hydrate. When the medicament of the present invention is blended with a stabilizer, the content thereof can be appropriately adjusted depending on the type and the like of the stabilizer, preferably 0.001 to 1% (w/v), more preferably 0.005 to 0.5% (w/v), and most preferably 0.01 to 0.1% (w/v).

The medicament of the present invention can be appropriately blended with a preservative that can be used as an additive for a pharmaceutical preparation.

Examples of the preservative include benzalkonium chloride, benzalkonium bromide, benzethonium chloride, sorbic acid, potassium sorbate, methyl paraoxybenzoate, propyl paraoxybenzoate, chlorobutanol, and the like. When the medicament of the present invention is blended with a preservative, the content thereof can be appropriately adjusted depending on the type and the like of the preservative, and is preferably 0.0001 to 1% (w/v), more preferably 0.0005 to 0.1% (w/v), further preferably 0.001 to 0.05% (w/v), and most preferably 0.005 to 0.010% (w/v). Moreover, the case where a preservative is not contained is also preferable.

The medicament of the present invention can be appropriately blended with an antioxidant that can be used as an additive for a pharmaceutical preparation.

Examples of the antioxidant include ascorbic acid, tocophenol, dibutylhydroxytoluene, butylhydroxyanisole, sodium erythorbate, propyl gallate, sodium sulfite, and the like. When the medicament of the present invention is blended with an antioxidant, the content thereof can be appropriately adjusted depending on the type and the like of the antioxidant, and is preferably 0.0001 to 1% (w/v), more preferably 0.0005 to 0.1% (w/v), and most preferably 0.001 to 0.05% (w/v).

The medicament of the present invention can be appropriately blended with a thickener that can be used as an additive for a pharmaceutical preparation.

Examples of the thickener include methyl cellulose, ethyl cellulose, hydroxymethyl cellulose, hydroxyethyl cellulose, hydroxypropyl cellulose, hydroxyethyl methyl cellulose, hydroxypropyl methyl cellulose, carboxymethyl cellulose, sodium carboxymethyl cellulose, hydroxypropyl methylcellulose acetate succinate, hydroxypropyl methylcellulose phthalate, carboxymethylethylcellulose, cellulose acetate phthalate, polyvinyl pyrrolidone, polyvinyl alcohol, carboxyvinyl polymer, polyethylene glycol, and the like.

When the medicament of the present invention is blended with a thickener, the content thereof can be appropriately adjusted depending on the type and the like of the thickener, and is preferably 0.001 to 5% (w/v), more preferably 0.01 to 1% (w/v), and most preferably 0.1 to 0.5% (w/v).

The medicament of the present invention can be appropriately blended with a base that can be used as an additive for a pharmaceutical preparation.

Examples of the base include water, physiological saline, dimethyl sulfoxide, polyethylene glycols such as PEG 400, tributyl citrate, acetyltributyl citrate, benzyl benzoate, white petrolatum, liquid paraffin, and the like, and water, physiological saline, dimethyl sulfoxide, and PEG 400 are preferable.

The pH of the medicament of the present invention is preferably 4.0 to 8.0, more preferably 4.5 to 7.5, particularly preferably 5.0 to 7.0, especially preferably 5.5 to 6.5, and most preferably 5.5 to 6.1. In addition, the pH may be 6.0 to 8.0. The medicament of the present invention may be added with a PH adjuster for adjusting the pH, such as hydrochloric acid, phosphoric acid, citric acid, acetic acid, sodium hydroxide, and potassium hydroxide

[Usage]

The medicament in the present invention is useful for retinal vasodilation, retinal nerve cell protection, and/or retinal blood flow improvement. Here, the "retinal nerve cell" means a nerve cell involved in the transmission of a visual signal to the brain. Specific examples include photoreceptor cells, bipolar cells, retinal ganglion cells, horizontal cells, and amacrine cells.

The "retinal nerve cell protection" in the present invention not only means to suppress the death of retinal nerve cells and/or the decrease in retinal nerve cell functions triggered by any cause including a decrease in blood flow in retinal blood vessels, but also means to prevent the death of retinal nerve cells and/or the decrease in retinal nerve cell functions that may occur in the future.

The "retinal blood flow improvement" in the present invention means a phenomenon of increasing the blood flow rate in retinal tissues and blood vessels that feed the retinal tissues. Specifically, the retinal blood flow improvement means to increase blood flow rate in the ophthalmic artery, the long posterior ciliary arteries, the short posterior ciliary arteries, the central retinal artery, the retinal blood vessels, the retinal tissue, the optic nerve head tissue, and the like.

Note that, in general, the increase in blood flow rate can be caused not only by vasodilation, but also by an increase in blood flow fluidity and an increase in blood flow velocity.

The medicament of the present invention can be used for prevention and/or treatment of ophthalmic diseases. Here, the "ophthalmic diseases" in the present invention include all diseases relating to the eye, but mainly mean ophthalmic diseases involving retinal nerve cell disorder and/or retinal blood flow. Specific examples include visual field abnormality, retinal vascular occlusion, diabetic retinopathy, ischemic optic neuropathy, glaucoma, glaucomatous optic neuropathy, glaucomatous visual field stenosis, glaucomatous optic nerve atrophy, PPG (Preperimetoric glaucoma), optic neuropathy caused by insufficiency of blood circulation, macular degeneration, retinitis pigmentosa, Leber's disease, retinopathy of prematurity, retinal detachment, and retinal pigment epithelial detachment, and visual field abnormality, ischemic optic neuropathy, glaucoma, glaucomatous optic neuropathy, glaucomatous visual field stenosis, glaucomatous optic nerve atrophy, and optic neuropathy caused by insufficiency of blood circulation are preferable.

Note that patients targeted by the medicament of the present invention are mammals including domestic animals such as cows and pigs, rabbits, monkeys, dogs, cats, and humans, and preferably humans.

[Route of Administration]

The medicament of the present invention can be administered orally or parenterally, such as ophthalmic administration, intravitreal administration, conjunctival sac administration, intracameral administration, subconjunctival administration, subtenon sac administration, or punctal plug administration. The dosage form of the medicament of the present invention includes ophthalmic solutions, ophthalmic ointments, injections, punctal plugs, tablets, capsules, granules, powders, and the like, and ophthalmic solutions, ophthalmic injections, and punctal plugs are particularly preferable. The ophthalmic injections include injections for intravitreal administration, intracameral administration, conjunctival sac administration, intracameral administration, subconjunctival administration, or subtenon administration. The dosage form of the medicament of the present invention can be produced according to conventional methods in the technical field of drugs. In addition to the above-described additives, oral formulations such as tablets, capsules, granules, and powders can be formulated by using, as necessary, bulking agents such as lactose, crystalline cellulose, starch, and vegetable oil, lubricants such as magnesium stearate and talc, binders such as hydroxypropylcellulose and polyvinylpyrrolidone, disintegrators such as carboxymethylcellulose calcium and low-substituted hydroxypropyl methylcellulose, coating agents such as hydroxypropyl methylcellulose, macrogol, and silicone resin, filmed medicines such as gelatin coating, and the like.

The medicament of the present invention can be stored in containers made of various materials. For example, containers made of polyethylene, polypropylene, and the like can be used, and in the case of use as an ophthalmic solution, the medicament of the present invention is preferably stored in a polyethylene container from the viewpoint of e.g. ease of instillation (hardness of the container) and stability of the present compound.

[Dosage and Administration]

The dosage and administration of the medicament of the present invention are not particularly limited as long as they are dosage and administration sufficient to produce the desired efficacy, and can be appropriately selected according to the symptoms of the disease, the age and weight of the patient, the dosage form of the medicament, and the like.

Specifically, in the case of an ophthalmic solution, one to five drops, preferably one to three drops, more preferably one or two drops, and particularly preferably one drop per dose may be ophthalmically administered one to four times a day, preferably one to three times a day, more preferably once or twice a day, and particularly once a day with a frequency of every day to every week. It is preferable that the ophthalmic solution be ophthalmically administered at one drop once a day every day. Here, one drop is usually about 0.01 to about 0.1 mL, preferably about 0.015 to about 0.07 mL, more preferably about 0.02 to about 0.05 mL, and particularly preferably about 0.03 mL.

In the case of an ophthalmic injection, it is preferably 1 to 1000 µL, more preferably 5 to 700 µL, further preferably 10 to 500 µL, and most preferably 20 to 300 µL at a time. The dose of the drug is preferably 0.0001 to 30000 µg/eye, more preferably 0.0005 to 10000 µg/eye, and most preferably 0.001 to 5000 µg/eye. When the medicament of the present invention is continuously administered as an ophthalmic injection, there is no particular limitation on the administration interval as long as it is sufficient to produce the desired efficacy. However, the administration interval is preferably once a week to once every three years, the administration interval is more preferably once a week, once every two weeks, once a month, once every two months, once every three months, once every four months, once every five months, once every six months, once a year, once every two years, or once every three years, and most preferably once every two months, once every three months, once every four months, once every five months or once every six months. In addition, the administration interval can be appropriately changed.

In the case of an oral preparation, it can be administered at 0.01 to 5000 mg, and preferably 0.1 to 1000 mg per day in one to several times separately (two to five times, preferably two or three times).

The above detailed description on the medicament of the present invention also applies to omidenepag, an ester thereof, or a salt thereof for use in prevention and/or treatment of an ophthalmic disease of the present invention, a method of preventing and/or treating an ophthalmic disease, comprising administering to a patient a medicament containing omidenepag, an ester thereof, or a salt thereof as an active ingredient, a method of producing a medicament for retinal vasodilatory action, retinal nerve cell protection, and/or retinal blood flow improvement, comprising formulating omidenepag, an ester thereof, or a salt thereof as an active ingredient, and use of omidenepag, an ester thereof, or a salt thereof for producing a medicament for retinal vasodilatory action, retinal nerve cell protection, and/or retinal blood flow improvement.

Examples relating to Formulation Examples and pharmacological test results of the present invention are presented below. Note that these examples are for better understanding of the present invention, and do not limit the scope of the present invention.

EXAMPLES

Formulation Example

The omidenepag, an ester thereof, or a salt thereof of the present invention can be used for the production of the medicament as described above. Tables 1 to 12 below present representative formulation examples (Formulation Examples 1 to 120) of the medicament (ophthalmic solution) of the present invention. In addition, Formulation Examples 121 and 122 present representative formulation examples of the medicament (injection) of the present invention.

Note that, in the following formulation examples, the amount of each of the ingredients is the content in 100 mL of the formulation.

Ophthalmic Solution (in 100 mL)

TABLE 1

| Formulation Example | 1 | 2 | 3 | 4 | 5 | 6 | 7 | 8 | 9 | 10 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.1 g | 0.1 g | 0.1 g | 0.1 g | 0.1 g | 0.5 g | 0.5 g | 0.5 g | 0.5 g | 0.5 g |
| Disodium Edetate | 0.01 g | 0.01 g | 0.01 g | 0.01 g | 0.01 g | 0.01 g | 0.01 g | 0.01 g | 0.01 g | 0.01 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0 g | 0 g | 0 g | 0 g | 0 g | 0 g | 0 g | 0 g | 0 g | 0 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 2

| Formulation Example | 11 | 12 | 13 | 14 | 15 | 16 | 17 | 18 | 19 | 20 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.8 g | 0.8 g | 0.8 g | 0.8 g | 0.8 g | 1.0 g | 1.0 g | 1.0 g | 1.0 g | 1.0 g |
| Disodium Edetate | 0.01 g | 0.01 g | 0.01 g | 0.01 g | 0.01 g | 0.01 g | 0.01 g | 0.01 g | 0.01 g | 0.01 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0 g | 0 g | 0 g | 0 g | 0 g | 0 g | 0 g | 0 g | 0 g | 0 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 3

| Formulation Example | 21 | 22 | 23 | 24 | 25 | 26 | 27 | 28 | 29 | 30 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.1 g | 0.1 g | 0.1 g | 0.1 g | 0.1 g | 0.5 g | 0.5 g | 0.5 g | 0.5 g | 0.5 g |
| Disodium Edetate | 0.01 g | 0.01 g | 0.01 g | 0.01 g | 0.01 g | 0.01 g | 0.01 g | 0.01 g | 0.01 g | 0.01 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.005 g | 0.005 g | 0.005 g | 0.005 g | 0.005 g | 0.005 g | 0.005 g | 0.005 g | 0.005 g | 0.005 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 4

| Formulation Example | 31 | 32 | 33 | 34 | 35 | 36 | 37 | 38 | 9 | 40 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.8 g | 0.8 g | 0.8 g | 0.8 g | 0.8 g | 1.0 g | 1.0 g | 1.0 g | 1.0 g | 1.0 g |
| Disodium Edetate | 0.01 g | 0.01 g | 0.01 g | 0.01 g | 0.01 g | 0.01 g | 0.01 g | 0.01 g | 0.01 g | 0.01 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.005 g | 0.005 g | 0.005 g | 0.005 g | 0.005 g | 0.005 g | 0.005 g | 0.005 g | 0.005 g | 0.005 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 5

| Formulation Example | 41 | 42 | 43 | 44 | 45 | 46 | 47 | 48 | 49 | 50 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.1 g | 0.1 g | 0.1 g | 0.1 g | 0.1 g | 0.5 g | 0.5 g | 0.5 g | 0.5 g | 0.5 g |
| Disodium Edetate | 0.01 g | 0.01 g | 0.01 g | 0.01 g | 0.01 g | 0.01 g | 0.01 g | 0.01 g | 0.01 g | 0.01 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.01 g | 0.01 g | 0.01 g | 0.01 g | 0.01 g | 0.01 g | 0.01 g | 0.01 g | 0.01 g | 0.01 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 6

| Formulation Example | 51 | 52 | 53 | 54 | 55 | 56 | 57 | 58 | 59 | 60 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.8 g | 0.8 g | 0.8 g | 0.8 g | 0.8 g | 1.0 g | 1.0 g | 1.0 g | 1.0 g | 1.0 g |
| Disodium Edetate | 0.01 g | 0.01 g | 0.01 g | 0.01 g | 0.01 g | 0.01 g | 0.01 g | 0.01 g | 0.01 g | 0.01 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.01 g | 0.01 g | 0.01 g | 0.01 g | 0.01 g | 0.01 g | 0.01 g | 0.01 g | 0.01 g | 0.01 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 7

| Formulation Example | 61 | 62 | 63 | 64 | 65 | 66 | 67 | 68 | 69 | 70 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.1 g | 0.1 g | 0.1 g | 0.1 g | 0.1 g | 0.5 g | 0.5 g | 0.5 g | 0.5 g | 0.5 g |
| Disodium Edetate | 0.02 g | 0.02 g | 0.02 g | 0.02 g | 0.02 g | 0.02 g | 0.02 g | 0.02 g | 0.02 g | 0.02 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0 g | 0 g | 0 g | 0 g | 0 g | 0 g | 0 g | 0 g | 0 g | 0 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |

TABLE 7-continued

| Formulation Example | 61 | 62 | 63 | 64 | 65 | 66 | 67 | 68 | 69 | 70 |
|---|---|---|---|---|---|---|---|---|---|---|
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 8

| Formulation Example | 71 | 72 | 73 | 74 | 75 | 76 | 77 | 78 | 79 | 80 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.8 g | 0.8 g | 0.8 g | 0.8 g | 0.8 g | 1.0 g | 1.0 g | 1.0 g | 1.0 g | 1.0 g |
| Disodium Edetate | 0.02 g | 0.02 g | 0.02 g | 0.02 g | 0.02 g | 0.02 g | 0.02 g | 0.02 g | 0.02 g | 0.02 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0 g | 0 g | 0 g | 0 g | 0 g | 0 g | 0 g | 0 g | 0 g | 0 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 9

| Formulation Example | 81 | 82 | 83 | 84 | 85 | 86 | 87 | 88 | 89 | 90 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.1 g | 0.1 g | 0.1 g | 0.1 g | 0.1 g | 0.5 g | 0.5 g | 0.5 g | 0.5 g | 0.5 g |
| Disodium Edetate | 0.02 g | 0.02 g | 0.02 g | 0.02 g | 0.02 g | 0.02 g | 0.02 g | 0.02 g | 0.02 g | 0.02 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.005 g | 0.005 g | 0.005 g | 0.005 g | 0.005 g | 0.005 g | 0.005 g | 0.005 g | 0.005 g | 0.005 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 10

| Formulation Example | 91 | 92 | 93 | 94 | 95 | 96 | 97 | 98 | 99 | 100 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.8 g | 0.8 g | 0.8 g | 0.8 g | 0.8 g | 1.0 g | 1.0 g | 1.0 g | 1.0 g | 1.0 g |
| Disodium Edetate | 0.02 g | 0.02 g | 0.02 g | 0.02 g | 0.02 g | 0.02 g | 0.02 g | 0.02 g | 0.02 g | 0.02 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.005 g | 0.005 g | 0.005 g | 0.005 g | 0.005 g | 0.005 g | 0.005 g | 0.005 g | 0.005 g | 0.005 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 11

| Formulation Example | 101 | 102 | 103 | 104 | 105 | 106 | 107 | 108 | 109 | 110 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |

TABLE 11-continued

| Formulation Example | 101 | 102 | 103 | 104 | 105 | 106 | 107 | 108 | 109 | 110 |
|---|---|---|---|---|---|---|---|---|---|---|
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.1 g | 0.1 g | 0.1 g | 0.1 g | 0.1 g | 0.5 g | 0.5 g | 0.5 g | 0.5 g | 0.5 g |
| Disodium Edetate | 0.02 g | 0.02 g | 0.02 g | 0.02 g | 0.02 g | 0.02 g | 0.02 g | 0.02 g | 0.02 g | 0.02 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.01 g | 0.01 g | 0.01 g | 0.01 g | 0.01 g | 0.01 g | 0.01 g | 0.01 g | 0.01 g | 0.01 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

TABLE 12

| Formulation Example | 111 | 112 | 113 | 114 | 115 | 116 | 117 | 118 | 119 | 120 |
|---|---|---|---|---|---|---|---|---|---|---|
| Omidenepag Isopropyl | 0.002 g | 0.002 g | 0.002 g | 0.002 g | 0.002 g | 0.002 g | 0.002 g | 0.002 g | 0.002 g | 0.002 g |
| Trisodium Citrate Dihydrate | 0.10 g | 0.12 g | 0.14 g | 0.16 g | 0.18 g | 0.09 g | 0.11 g | 0.13 g | 0.15 g | 0.17 g |
| Citric Acid Monohydrate | 0.05 g | 0.04 g | 0.03 g | 0.02 g | 0.01 g | 0.05 g | 0.04 g | 0.03 g | 0.02 g | 0.01 g |
| Polyoxyl 35 Castor Oil | 0.8 g | 0.8 g | 0.8 g | 0.8 g | 0.8 g | 1.0 g | 1.0 g | 1.0 g | 1.0 g | 1.0 g |
| Disodium Edetate | 0.02 g | 0.02 g | 0.02 g | 0.02 g | 0.02 g | 0.02 g | 0.02 g | 0.02 g | 0.02 g | 0.02 g |
| Glycerin | 2.3 g | 2.3 g | 2.3 g | 2.3 g | 2.3 g | 2.7 g | 2.7 g | 2.7 g | 2.7 g | 2.7 g |
| Benzalkonium Chloride | 0.01 g | 0.01 g | 0.01 g | 0.01 g | 0.01 g | 0.01 g | 0.01 g | 0.01 g | 0.01 g | 0.01 g |
| Sodium Hydroxide | q.s. | q.s. | q.s. | q.s. | q.s. | q.s. | q.s. | q.s. | q.s. | q.s. |
| Hydrochloric Acid | q.s. | q.s. | q.s. | q.s. | q.s. | q.s. | q.s. | q.s. | q.s. | q.s. |
| Purified Water | q.s. | q.s. | q.s. | q.s. | q.s. | q.s. | q.s. | q.s. | q.s. | q.s. |
| pH | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 | 5.5 to 6.1 |

Formulation Example 121

| Injection 1 (in 100 mL) | |
|---|---|
| Omidenepag | 0.003 g |
| PEG 400 | quantum sufficit |

Formulation Example 122

| Injection 2 (in 100 mL) | |
|---|---|
| Omidenepag | 0.0003 g |
| PEG 400 | quantum sufficit |

Note that, in Formulation Examples 1 to 122, the desired medicament can be obtained by appropriately adjusting the type and/or amount blended of omidenepag and/or additive. In particular, the desired medicament can be obtained by setting the amount blended of omidenepag in Formulation Examples 1 to 122 to 0.001 g, 0.0011 g, 0.0012 g, 0.0013 g, 0.0014 g, 0.0015 g, 0.0016 g, 0.0017 g, 0.0018 g, 0.0019 g, 0.0021 g, 0.0022 g, 0.0023 g, 0.0024 g, 0.0025 g, 0.0026 g, 0.0027 g, 0.0028 g, 0.0029 g, or 0.003 g instead of 0.002 g.

[Pharmacological Test 1]

In order to find a new medicinal use of omidenepag, an ester thereof, or a salt thereof, the retinal vasodilatory action in the case of administering omidenepag to rabbits was examined.

(Preparation of Test Compound Solutions)

1) Preparation of Base A

Physiological saline at 16 mL was added and dissolved into 20 μL of dimethyl sulfoxide. After dissolution, a 0.1 mol/L sodium hydroxide solution was added to adjust the pH of the formulation to 7.2, and then physiological saline was added to a total volume of 20 mL to obtain a base A.

2) Preparation of Omidenepag Samples 1 and 2

Omidenepag at 4.01 mg was dissolved in dimethyl sulfoxide to a total volume of 129 μL. Of the total volume, 10 μL was added and dissolved into physiological saline, and an appropriate amount of sodium hydroxide solution was added to adjust the pH of the formulation to 6.2. Thereafter, physiological saline was further added to a total volume of 10 mL to obtain omidenepag sample 1 (containing 0.00311% (w/v) (31.1 μg/mL) of omidenepag). In addition, the base A was added to 0.1 mL of omidenepag sample 1 to a total volume of 10 mL, and omidenepag sample 2 was obtained (containing 0.0000311% (w/v) (0.311 μg/mL) of omidenepag).

3) Preparation of CP-544326 Samples 1 and 2

CP-544326 (EP2 agonist) at 5.98 mg was dissolved in dimethyl sulfoxide to a total volume of 192 μL. Of the total volume, 10 μL was added and dissolved into physiological saline, and sodium hydroxide solution was added to adjust the pH of the formulation to 6.5. Thereafter, physiological saline was further added to a total volume of 10 mL to obtain CP-544326 sample 1 (containing 0.00311% (w/v) (31.1 μg/mL) of CP-544326). In addition, the base A was added to 0.1 mL of CP-544326 sample 1 to a total volume of 10 mL, and CP-544326 sample 2 was obtained (containing 0.0000311% (w/v) (0.311 μg/mL) of CP-544326).

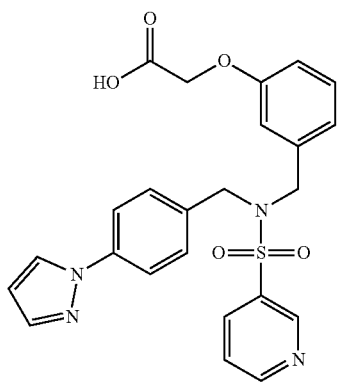
(CP-544326)

(Test Method)

The base A, omidenepag samples 1 and 2, and CP-544326 samples 1 and 2 as test compound solutions, each at 20 µL, were administered intravitreally (injection, single time) to examine the change in retinal vascular diameter. In addition, pigmented rabbits (strain: Dutch, sex: male, three animals per group) were used as experimental animals.

(Method of Administering Test Compound Solutions and Method of Measuring Retinal Vascular Diameter)

1) After holding the above experimental animals, one drop (about 0.03 mL) of a 0.4% tropicamide ophthalmic solution (trade name: Mydrin-M ophthalmic solution 0.4%) was instilled into the retinal vascular diameter measurement eye to fully dilate the pupil. Thereafter, fundus images of the measurement eyes were captured, and the retinal vascular diameters and the like immediately before administration were measured from the obtained fundus images.

2) One drop (about 0.03 mL) of a 0.4% oxybuprocaine hydrochloride ophthalmic solution (trade name: Benoxil ophthalmic solution 0.4%) was instilled into the retinal vascular diameter measurement eye of each experimental animal for local anesthesia. Thereafter, a microsyringe connected with a 30 G injection needle was used to administer 20 µL of each test compound solution into the vitreous body.

3) At 1 hour, 2 hours, 6 hours, and 24 hours after administration of each test compound solution, fundus images of the retinal vascular diameter measuring eyes were captured, and the retinal vascular diameters and the like were measured from the obtained fundus images.

(Method of Calculating Base-Corrected Retinal Vascular Diameter Change Rate)

(a) The fundus images captured immediately before the administration, 1 hour, 2 hours, 6 hours, and 24 hours after the administration were used to measure, as the vascular diameters, (i) the vascular diameter of the retinal artery on the nose side, (ii) the vascular diameter of the retinal artery on the ear side, and (iii) the optic nerve head diameter (longitudinal diameter passing through the center of the optic nerve head).

(b) The average value of (i) the vascular diameter of the retinal artery on the nose side and (ii) the vascular diameter of the retinal artery on the ear side measured from the fundus images for each time period was divided by (iii) the optic nerve head diameter to calculate the corrected retinal vascular diameter.

[Corrected Retinal Vascular Diameter]=(([(i) Vascular Diameter of Retinal Artery on Nose Side]+ [(ii) Vascular Diameter of Retinal Artery on Ear Side])/2)/([(iii) Optic Nerve Head Diameter])

(c) The ratio of the corrected retinal vascular diameter after passage of each of the time periods of 1 hour, 2 hours, 6 hours, and 24 hours after administration to the corrected retinal vascular diameter immediately before administration (retinal vascular diameter change rate (%)) was calculated.

[Retinal Vascular Diameter Change Rate (%) After Passage of Each Time Period After Administration]=[Corrected Retinal Vascular Diameter After Passage of Each Time Period After Administration]/[Corrected Retinal Vascular Diameter Immediately Before Administration]× 100

(d) For each time period after administration, the difference (base-corrected retinal vascular diameter change rate (%)) was calculated between the retinal vascular diameter change rate (%) of the group administered with the base simultaneously carried out and the retinal vascular diameter change rate (%) of the groups administered with samples (omidenepag samples 1 and 2, and CP-544326 samples 1 and 2).

[Base-Corrected Retinal Vascular Diameter Change Rate (%) After Passage of Each Time Period]= [Retinal Vascular Diameter Change Rate (%) After Passage of Each Time Period After Administration of Samples]−[Retinal Vascular Diameter Change Rate (%) After Passage of Each Time Period After Administration of Base]

(e) The base-corrected retinal vascular diameter change rate (%) of (a) to (d) above was calculated for three experimental animals in each group, and the average thereof was defined as the value of the "base-corrected retinal vascular diameter change rate (%)."

(Results)

Table 13 presents the average of the base-corrected retinal vascular diameter change rate (%) after administration of each sample.

TABLE 13

| | | Base-Corrected Retinal Vascular Diameter Change Rate (%) | | | |
|---|---|---|---|---|---|
| Sample | Concentration | 1 Hour After Administration | 2 Hours After Administration | 6 Hours After Administration | 24 Hours After Administration |
| Omidenepag Sample 1 | 0.00311% (w/v) (31.1 µg/mL) | 81.2 | 71.9 | 88.1 | 11.8 |
| Omidenepag Sample 2 | 0.0000311% (w/v) (0.311 µg/mL) | 35.8 | 35.4 | 22.3 | 2.9 |
| CP-544326 Sample 1 | 0.00311% (w/v) (31.1 µg/mL) | 48.4 | 57.5 | 72.2 | 3.7 |

TABLE 13-continued

| | | Base-Corrected Retinal Vascular Diameter Change Rate (%) | | | |
|---|---|---|---|---|---|
| Sample | Concentration | 1 Hour After Administration | 2 Hours After Administration | 6 Hours After Administration | 24 Hours After Administration |
| CP-544326 Sample 2 | 0.0000311% (w/v) (0.311 µg/mL) | 14.8 | 9.0 | 0.8 | 3.5 |

As is apparent from Table 13, omidenepag exhibited a significantly stronger retinal vasodilatory action (increase in the base-corrected retinal vascular diameter change rate) than CP-544326 at the same concentration.

It has been found from the above that omidenepag, an ester thereof, or a salt thereof can significantly dilate retinal blood vessels and moreover significantly increase blood flow rate as compared with other EP2 agonists. In addition, it has been found that an effect of improving retinal blood flow can be expected due to a significant increase in the blood flow rate of retinal blood vessels resulting from the effect of significant dilatation of retinal blood vessels, and moreover that an effect can be expected of suppressing the death of retinal nerve cells and/or the decrease in retinal nerve cell functions, and protecting retinal nerve cells.

(Test Method)

In the same method as that in Pharmacological Test 1, the base B and omidenepag isopropyl samples 1 and 2, each at 20 µL, were administered intravitreally (injection, single time) to examine the change in retinal vascular diameter. Note that, 1 hour, 2 hours, 6 hours, 24 hours, and 48 hours after administration of each test compound solution, fundus images of the retinal vascular diameter measuring eyes were captured, and the retinal vascular diameters and the like were measured from the obtained fundus images. In addition, pigmented rabbits (strain: Dutch, sex: male, three animals per group) were used as the rabbits as experimental animals.

(Results)

Table 14 presents the average of the base-corrected retinal vascular diameter change rate (%) after administration of each sample.

TABLE 14

| | | Base-Corrected Retinal Vascular Diameter Change Rate (%) | | | | |
|---|---|---|---|---|---|---|
| Sample | Concentration | 1 Hour After Administration | 2 Hours After Administration | 6 Hours After Administration | 24 Hours After Administration | 48 Hours After Administration |
| Omidenepag Isopropyl Sample 1 | 0.00338% (w/v) (33.8 µg/mL) | 58.4 | 81.7 | 73.8 | 16.0 | 0.0 |
| Omidenepag Isopropyl Sample 2 | 0.0000338% (w/v) (0.338 µg/mL) | 25.1 | 34.5 | 18.4 | 6.8 | 1.7 |

[Pharmacological Test 2]

In order to find anew medicinal use of omidenepag, an ester thereof, or a salt thereof, the retinal vasodilatory action in the case of administering omidenepag isopropyl to rabbits was examined.

(Preparation of Test Compound Solutions)

1) Preparation of Base B

Physiological saline at 16 mL was added and dissolved into 20 µL of dimethyl sulfoxide. After dissolution, a 0.1 mol/L sodium hydroxide solution was added to adjust the pH of the formulation to 7.0, and then physiological saline was added to a total volume of 20 mL to obtain a base B.

2) Preparation of Omidenepag Isopropyl Samples 1 and 2

Omidenepag isopropyl at 3.98 mg was dissolved in dimethyl sulfoxide to a total volume of 118 µL. Of the total volume, 10 µL was added and dissolved into physiological saline, and an appropriate amount of sodium hydroxide solution was added to adjust the pH of the formulation to 6.4. Thereafter, physiological saline was further added to a total volume of 10 mL to obtain omidenepag isopropyl sample 1 (containing 0.00338% (w/v) (33.8 µg/mL) of omidenepag isopropyl). In addition, the base B was added to 0.1 mL of omidenepag isopropyl sample 1 to a total volume of 10 mL, and omidenepag isopropyl sample 2 was obtained (containing 0.0000338% (w/v) (0.338 µg/mL) of omidenepag isopropyl).

As is apparent from Table 14, omidenepag isopropyl also exhibited a significantly strong retinal vasodilatory action (increase in the base-corrected retinal vascular diameter change rate). In addition, although omidenepag isopropyl 0.0033800 (w/v) and omidenepag 0.00311% (w/v) were both 65.0 µM, the former still exhibited a base-corrected retinal vascular diameter change rate of 16.0% even 24 hours after administration. Therefore, omidenepag isopropyl had amore durable action than omidenepag (Table 13: base-corrected retinal vascular diameter change rate of 11.8).

[Pharmacological Test 3]

In order to find anew medicinal use of omidenepag, an ester thereof, or a salt thereof, the action of increasing tissue blood flow in the optic nerve head in the case of administering omidenepag to rabbits was examined.

(Preparation of Test Compound Solutions)

1) Preparation of Base C (Three-Time Preparation)

Physiological saline at 16 mL was added and dissolved into 20 µL of dimethyl sulfoxide. After dissolution, a 0.1 mol/L sodium hydroxide solution was added to adjust the pH of the formulation to 6.4 to 7.2, and then physiological saline was added to a total volume of 20 mL to obtain a base C.

2) Preparation of Omidenepag Sample 3 (Three-Time Preparation)

Omidenepag at 3.99 to 4.03 mg was dissolved in dimethyl sulfoxide to a total volume of 128 to 130 μL. Of the total volume, 10 μL was added and dissolved into physiological saline, and an appropriate amount of sodium hydroxide solution was added to adjust the pH of the formulation to 6.3 to 7.2. Thereafter, physiological saline was further added to a total volume of 10 mL to obtain omidenepag sample 3 (containing 0.00311% (w/v) (31.1 μg/mL) of omidenepag).

(Test Method)

The base C and omidenepag sample 3 as test compound solutions, each at 20 μL, were administered intravitreally (injection, single time) to examine the change in optic nerve head tissue blood flow. In addition, pigmented rabbits (strain: Dutch, sex: male, three animals per group) were used as experimental animals.

(Method of Administering Test Compound Solutions and Optic Nerve Head Tissue Blood Flow Method)

1) After holding the above experimental animals, one drop (about 0.03 mL) of a 0.4% tropicamide ophthalmic solution (trade name: Mydrin-M ophthalmic solution 0.4%) was instilled into the optic nerve head tissue blood flow measurement eye to fully dilate the pupil. Thereafter, laser speckle flowgraphy (LSFG-NAVI manufactured by Softcare Co., Ltd.) was used to measure the tissue blood flow in the optic nerve head of the measurement eye.

2) One drop (about 0.03 mL) of a 0.4% oxybuprocaine hydrochloride ophthalmic solution (trade name: Benoxil ophthalmic solution 0.4%) was instilled into the optic nerve head tissue blood flow measurement eye of each experimental animal for local anesthesia. Thereafter, a microsyringe connected with a 30 G injection needle was used to administer 20 μL of each test compound solution into the vitreous body.

3) At 1 hour and 2 hours after administration of each test compound solution, the optic nerve head tissue blood flow of the optic nerve head tissue blood flow measurement eye was measured.

(Method of Calculating Base-Corrected Optic Nerve Head Tissue Blood Flow Change Rate)

(a) The ratio of the optic nerve head tissue blood flow after passage of each of the time periods of 1 hour and 2 hours after administration to the optic nerve head tissue blood flow immediately before administration (optic nerve head tissue blood flow change rate (%)) was calculated.

[Optic Nerve Head Tissue Blood Flow Change Rate (%) After Passage of Each Time Period After Administration]=[Optic Nerve Head Tissue Blood Flow After Passage of Each Time Period After Administration]/[Optic Nerve Head Tissue Blood Flow Immediately Before Administration]×100

(b) For each time period after administration, the difference (base-corrected optic nerve head tissue blood flow change rate (%)) was calculated between the optic nerve head tissue blood flow change rate (%) of the group administered with the base C simultaneously carried out and the optic nerve head tissue blood flow change rate (%) of the group administered with omidenepag sample 3.

[Base-Corrected Optic Nerve Head Tissue Blood Flow Change Rate (%) After Passage of Each Time Period]=[Optic Nerve Head Tissue Blood Flow Change Rate (%) After Passage of Each Time Period After Administration of Omidenepag Sample 3]−[Optic Nerve Head Tissue Blood Flow Change Rate (%) After Passage of Each Time Period After Administration of Base C]

(c) The base-corrected optic nerve head tissue blood flow change rate (%) of (a) and (b) above was calculated for three experimental animals in each group, and the average thereof was defined as the value of the "base-corrected optic nerve head tissue blood flow change rate (%)."

(Results)

Table 15 presents the average of the base-corrected optic nerve head tissue blood flow change rate (%).

TABLE 15

| Sample | Concentration | Base-Corrected Optic Nerve Head Tissue Blood Flow Change Rate (%) | |
|---|---|---|---|
| | | 1 Hour After Administration | 2 Hours After Administration |
| Omidenepag Sample 3 | 0.00311% (w/v) (31.1 μg/mL) | 343.6 | 327.8 |

As is apparent from Table 15, omidenepag presented a significantly strong blood flow increasing action (increase in the base-corrected optic nerve head tissue blood flow change rate) by intravitreal administration.

[Pharmacological Test 4]

In order to find a new medicinal use of omidenepag, an ester thereof, or a salt thereof, the action of increasing tissue blood flow in the optic nerve head in the case of instilling omidenepag isopropyl to rabbits was examined.

(Preparation of Test Compound Solutions)

1) Preparation of Base D

Polyoxyl 35 castor oil, glycerin, sodium citrate, sodium edetate, and benzalkonium chloride were added and dissolved into purified water to adjust the pH. Thereafter, purified water was added to adjust the total volume.

2) Preparation of Omidenepag Isopropyl Sample 3

Omidenepag isopropyl, polyoxyl 35 castor oil, glycerin, sodium citrate, sodium edetate, and benzalkonium chloride were added and dissolved into purified water to adjust the pH. Thereafter, purified water was added to adjust the total volume, thereby preparing a 0.002 w/v % omidenepag isopropyl solution (omidenepag isopropyl sample 3).

(Test Method)

The base D and omidenepag isopropyl sample 3 as test compound solutions, each at 50 μL, were instilled (ophthalmic solution, once a day, repeated instillation for 14 days) to examine the change in optic nerve head tissue blood flow. In addition, pigmented rabbits (strain: Dutch, sex: male, four animals per group) were used as experimental animals.

(Method of Administering Test Compound Solutions and Optic Nerve Head Tissue Blood Flow Method)

1) After holding the above experimental animals, one drop (about 0.03 mL) of a 0.4% tropicamide ophthalmic solution (trade name: Mydrin-M ophthalmic solution 0.4%) was instilled into the optic nerve head tissue blood flow measurement eye to fully dilate the pupil. Thereafter, laser speckle flowgraphy (LSFG-NAVI manufactured by Softcare Co., Ltd.) was used to measure the tissue blood flow in the optic nerve head of the measurement eye.

2) The test compound solutions were instilled at 50 μL into one eye (optic nerve head tissue blood flow measurement eye) of each of the experimental animals once a day for 14 days (the contralateral eye was untreated).

3) At 1 hour and 2 hours after administration of each test compound solution at day 1, day 7, and day 14 after administration of each test compound solution, the optic nerve head tissue blood flow of the optic nerve head tissue blood flow measurement eye was measured.

(Method of Calculating Base-Corrected Optic Nerve Head Tissue Blood Flow Change Rate)

(a) The ratio of the optic nerve head tissue blood flow after passage of each of the time periods of 1 hour and 2 hours after administration of each test compound solution at day 1, day 7, and day 14 after the start of administration of each test compound solution to the optic nerve head tissue blood flow immediately before administration (optic nerve head tissue blood flow change rate (%)) was calculated.

[Optic Nerve Head Tissue Blood Flow Change Rate (%) After Passage of Each Time Period After Administration]=[Optic Nerve Head Tissue Blood Flow After Passage of Each Time Period After Administration]/[Optic Nerve Head Tissue Blood Flow Immediately Before Administration]×100

(b) For each time period after administration, the difference (base-corrected optic nerve head tissue blood flow change rate (%)) was calculated between the optic nerve head tissue blood flow change rate (%) of the group administered with the base D simultaneously carried out and the optic nerve head tissue blood flow change rate (%) of the group administered with omidenepag isopropyl sample 3.

[Base-Corrected Optic Nerve Head Tissue Blood Flow Change Rate (%) After Passage of Each Time Period]=[Optic Nerve Head Tissue Blood Flow Change Rate (%) After Passage of Each Time Period After Administration of Omidenepag Isopropyl Sample 3]−[Optic Nerve Head Tissue Blood Flow Change Rate (%) After Passage of Each Time Period After Administration of Base D]

(c) The base-corrected optic nerve head tissue blood flow change rate (%) of (a) and (b) above was calculated for four experimental animals in each group, and the average thereof was defined as the value of the "base-corrected optic nerve head tissue blood flow change rate (%)."

(Results)

Table 16 presents the average of the base-corrected optic nerve head tissue blood flow change rate (%).

TABLE 16

| | | Base-Corrected Optic Nerve Head Tissue Blood Flow Change Rate (%) | | | | | |
|---|---|---|---|---|---|---|---|
| | | Day 1 | | Day 7 | | Day 14 | |
| Sample | Concentration | 1 Hour After Administration | 2 Hours After Administration | 1 Hour After Administration | 2 Hours After Administration | 1 Hour After Administration | 2 Hours After Administration |
| Omidenepag Isopropyl Sample 3 | 0.002% (w/v) (20 µg/mL) | 7.2 | 6.3 | 9.9 | 12.4 | 13.6 | 11.5 |

As is apparent from Table 16, omidenepag isopropyl presented a good blood flow increasing action (increase in the base-corrected optic nerve head tissue blood flow change rate) by instillation.

It has been found from the above that omidenepag, an ester thereof, or a salt thereof can significantly dilate retinal blood vessels and moreover significantly increase blood flow rate as compared with other EP2 agonists. In addition, it has been found that an effect of improving retinal blood flow can be expected due to a significant increase in the blood flow rate of retinal blood vessels resulting from the effect of significant dilatation of retinal blood vessels, and moreover that an effect can be expected of suppressing the death of retinal nerve cells and/or the decrease in retinal nerve cell functions, and protecting retinal nerve cells.

What is claimed is:

1. A method of preventing and/or treating an ophthalmic disease, comprising administering to a patient a pharmaceutical composition containing omidenepag, an ester thereof, or a salt thereof as an active ingredient, wherein the ophthalmic disease is retinal vascular occlusion, diabetic retinopathy, ischemic optic neuropathy, optic neuropathy caused by insufficiency of blood circulation, macular degeneration, retinitis pigmentosa, Leber's disease, retinopathy of prematurity, retinal detachment, or retinal pigment epithelial detachment.

2. A method of producing a pharmaceutical composition for retinal vasodilatory action, retinal nerve cell protection, and/or retinal blood flow improvement for preventing and/or treating an ophthalmic disease, comprising formulating omidenepag, an ester thereof, or a salt thereof as an active ingredient, wherein the ophthalmic disease is retinal vascular occlusion, diabetic retinopathy, ischemic optic neuropathy, optic neuropathy caused by insufficiency of blood circulation, macular degeneration, retinitis pigmentosa, Leber's disease, retinopathy of prematurity, retinal detachment, or retinal pigment epithelial detachment.

3. The method according to claim 1, wherein a content of the omidenepag, the ester thereof, or the salt thereof in the pharmaceutical composition is 0.000001 to 30% (w/v).

4. The method according to claim 3, wherein the content of the omidenepag, the ester thereof, or the salt thereof in the pharmaceutical composition is 0.0015 to 10% (w/v).

5. The method according to claim 3, wherein the content of the omidenepag, the ester thereof, or the salt thereof in the pharmaceutical composition is 0.002% (w/v).

6. The method according to claim 1, wherein the omidenepag, the ester thereof, or the salt thereof is omidenepag isopropyl.

7. The method according to claim 1, wherein a route of administration is ophthalmic administration, intravitreal administration, conjunctival sac administration, intracameral administration, subconjunctival administration, sub-tenon administration, or punctal plug administration.

8. The method according to claim 7, wherein the route of administration is ophthalmic administration or intravitreal administration.

9. The method according to claim 1, wherein
a content of the omidenepag, the ester thereof, or the salt thereof is 0.0015 to 10% (w/v), and
a route of administration is ophthalmic administration or intravitreal administration.

10. The method according to claim 1, wherein
a content of the omidenepag, the ester thereof, or the salt thereof is 0.002% (w/v), and
a route of administration is ophthalmic administration.

11. A method of preventing and/or treating an ophthalmic disease, comprising administering to a patient a pharmaceutical composition containing omidenepag, an ester thereof, or a salt thereof as an active ingredient, wherein the ophthalmic disease is glaucoma, glaucomatous optic neuropathy, glaucomatous visual field stenosis, glaucomatous optic nerve atrophy or PPG (Preperimetoric glaucoma), and wherein a route of administration is intravitreal administration.

12. The method according to claim 11, wherein the content of the omidenepag, the ester thereof, or the salt thereof in the pharmaceutical composition is 0.000001 to 30% (w/v).

13. The method according to claim 11, wherein the omidenepag, the ester thereof, or the salt thereof is omidenepag isopropyl.

14. A method of preventing and/or treating an ophthalmic disease which is visual field abnormality, comprising administering to a patient a pharmaceutical composition containing omidenepag, an ester thereof, or a salt thereof as an active ingredient, wherein a route of administration is intravitreal administration.

15. The method according to claim 14, wherein a content of the omidenepag, the ester thereof, or the salt thereof in the pharmaceutical composition is 0.000001 to 30% (w/v).

16. The method according to claim 14, wherein the omidenepag, the ester thereof, or the salt thereof is omidenepag isopropyl.

* * * * *